US005422263A

United States Patent [19]
Zarlenga, Jr. et al.

[11] Patent Number: 5,422,263
[45] Date of Patent: Jun. 6, 1995

[54] **DNA ENCODING THE *TRICHINELLA SPIRALS* 53KD EXCRETORY/SECRETORY ANTIGEN FOR USE AS IMMUNODIAGNOSTIC REAGENTS**

[75] Inventors: Dante S. Zarlenga, Jr., Ellicott City; H. Ray Gamble, Bowie, both of Md.

[73] Assignee: The United States of America as represented by the Secretary of Agriculture, Washington, D.C.

[21] Appl. No.: 70,645

[22] Filed: Jun. 1, 1993

Related U.S. Application Data

[63] Continuation of Ser. No. 366,844, Jun. 15, 1989, abandoned.

[51] Int. Cl.$^6$ ............... C07K 15/28; C12N 15/30; C12P 21/08; A61K 39/002
[52] U.S. Cl. ............... 435/240.1; 424/191.1; 424/265.1; 435/69.3; 435/320.1; 435/172.3; 530/388.6; 536/23.1; 536/24.3
[58] Field of Search ............... 424/8, 191.1; 435/69.3, 435/240.1, 320.1, 172.3; 530/350.1, 387.6; 935/12; 536/23.1

[56] References Cited

U.S. PATENT DOCUMENTS 4,670,384  6/1987  Gamble et al. ............... 435/7

OTHER PUBLICATIONS

Sugane et al, J Helminthology 61(1), 1-8, (1987) Translation products of mRNA from infective larvae.
D. S. Zarlenga and H. R. Gamble, "Identification of cDNA Clones Expressing Immunodiagnostic Antigens from *Trichinella spiralis*," (Abstract), *Federation Proceedings* 46: 2038 (1987).
H. R. Gamble and C. E. Graham, "Monoclonal Antibody-Purified Antigen for the Immunodiagnosis of Trichinosis," *American Journal of Veterinary Research* 45:67-74 (1984).
H. R. Gamble, "*Trichinella spiralis*: Immunization of Mice Using Monoclonal Antibody Affinity-Isolated Antigens," *Experimental Parasitology* 59:398-400 (1985).
H. R. Gamble, W. R. Anderson, C. E. Graham and K. D. Murrell, "Diagnosis of Swine Trichinosis by Enzyme-Linked Immunosorbent Assay (ELISA) Using an Excretory-Secretory Antigen," *Veterinary Parasitology* 13:349-361 (1983).
G. L. Seawright et al., *American Journal of Tropical Med. Hyg.* 32:1275-1284 (1983).
D. S. Silberstein, "Studies on Antigens of Trichinella Spiralis," (Abstract), *Dissertation Abstracts International* 45:624-B (1984).
D. S. Silberstein and D. D. Despommier, "Antigens from *Trichinella spiralis* that Induce a Protective Response in the Mouse," *The Journal of Immunology* 132:898-904 (1984).
D. S. Zarlenga and H. R. Gamble, "Simultaneous Isolation of Preparative Amounts of RNA and DNA from *Trichinella spiralis* by Cesium Trifluoroacetate Isopycnic Centrifugation," *Analytical Biochemistry* 162:569-574 (1987).
G. R. Klassen, J. P. Thiessen and T. A. Dick, "Strain-Specific 1.7 Kilobase Repetitive Deoxyribonucleic Acid Sequence Family in *Trichinella spiralis*," *Molecular and Biochemical Parasitology* 21:227-233 (1986).
J. B. Dame, D. D. Murrell, D. E. Worley and G. A. Schad, "Trichinella spiralis: Genetic Evidence for Synanthropic Subspecies in Sylvatic Hosts," *Experimental Parasitology* 64:195-203 (1987).

*Primary Examiner*—David L. Lacey
*Assistant Examiner*—T. Michael Nisbet
*Attorney, Agent, or Firm*—M. Howard Silverstein; John D. Fado; Margaret A. Connor

[57] ABSTRACT

Disclosed are DNA sequences which encode an amino acid sequence homologous to a segment of *Trichinella spiralis* 53 kilodalton excretory-secretory antigen, recombinant polynucleotide molecules containing the sequences, and transfer and replication of the sequences in a transformed host to produce antigens useful as immunodiagnostic reagents or vaccines specific for *T. spiralis*.

9 Claims, 5 Drawing Sheets

DNA ENCODING THE *TRICHINELLA SPIRALS* 53KD EXCRETORY/SECRETORY ANTIGEN FOR USE AS IMMUNODIAGNOSTIC REAGENTS

This application is a continuation of application Ser. No. 07/366,844, filed Jun. 15, 1989, now abandoned.

BACKGROUND OF THE INVENTION

1. Field of the Invention

The present invention relates to DNA sequences which encode an amino acid sequence homologous to a segment of *Trichinella spiralis* 53 kilodalton (kD) excretory-secretory antigen, recombinant polynucleotide molecules containing the sequences, and transfer and replication of the sequences in a transformed host to produce antigens useful as immunodiagnostic reagents or vaccines specific for *T. spiralis*

2. Description of the Art

Trichinellosis (known historically as trichinosis), caused by the nematode parasite *Trichinella spiralis*, is an important zoonotic disease of world wide distribution. Trichinellosis results from the ingestion of raw or undercooked meat, generally pork, containing the infective larval stage of the parasite. An important component of a program to control or eradicate trichinellosis is a specific and sensitive diagnostic test. A variety of direct and indirect tests have been used for the diagnosis of trichinellosis in swine and other species, the most recent of which is the enzyme-linked immunosorbent assay (ELISA). Initially, ELISA tests were performed with crude extracts of *T. spiralis* is muscle larvae as antigen and resulted in a high number of false-positive reactions, apparently due to cross-reactions with other parasite infections. Subsequent replacement of the crude antigen preparation with biochemically purified stichocyte antigens (G. L. Seawright et al., *American Journal of Tropical Med. Hyg.* 32: 1275-1284, 1983), culture-derived excretory-secretory (ES) antigens (H. R. Gamble et al., *Veterinary Parasitology* 13: 349-361, 1983), or antibody affinity-purified ES antigens (H. R. Gamble and C. E. Graham, *American Journal of Veterinary Research* 45: 67-74, 1984) resulted in near elimination of false-positive reactions; however, inconsistencies in the yield and purity of antigen obtained by these procedures has remained a problem.

Use of naturally derived antigens to *T. spiralis* has several disadvantages. It requires continual passage of the parasites in laboratory rodents. The rodents must be sacrificed 30–40 days post-infection at which time the parasites are collected for antigen isolation, and additional rodents are infected for subsequent isolations. Thus, production of naturally derived antigens is both time consuming and costly. Further, both the yield and purity of material can vary significantly between preparations. What is needed is an economical way to provide an unlimited source of *T. spiralis* antigens having reliable and reproducible purity.

Limited information is available about *T. spiralis* antigens. *T. spiralis* muscle larvae have been shown to excrete and secrete antigens in culture which are useful as immnodiagnostic reagents (Gamble et al., 1983, supra). Immunodominant antigens in ES have been identified in the 45,000 to 53,000 molecular weight range. Similar molecular weight antigens have been extracted from *T. spiralis* stichocyte cells using biochemical procedures (D. S. Silberstein and D. D. Despommier, *The Journal of Immunology* 132:898-904, 1984). Monoclonal antibody generated from spleen cells of mice infected with *T. spiralis* recognized an antigenic determinant unique to *T. spiralis* present on proteins of molecular weights 45,000, 49,000, and 53,000 (Gamble and Graham, 1984, supra; H. R. Gamble, *Experimental Parasitology* 59: 398-404, 1985, and U.S. Pat. No. 4,670,384). Two of the proteins (49,000 and 53,000 molecular weight) possessing this determinant were isolated together by monoclonal antibody-affinity chromatography, and the affinity-isolated antigen used successfully in an ELISA for swine trichinellosis (Gamble and Graham, 1984, supra). *T. spiralis* antigens have been reported to be glycoproteins (Gamble, 1985, supra, and D. S. Silberstein, *Dissertation Abstracts International* 45: 824B, 1984). A 48 kD antigen, presumed homologous to the 45 kD antigen of Gamble and Graham, 1984, supra, has been partially characterized. However, no function for the proteins has been elucidated and biological activity has yet to be assigned. Further, no data has been made available indicating which stage of development the corresponding messenger RNA which codes for the antigen is produced.

An attempt to prepare *T. spiralis* diagnostic antigens by recombinant DNA techniques has been reported (Abstract, D. S. Zarlenga and H. R. Gamble, *Federation Proceedings* 46: 2038, 1987). The researchers prepared cDNA clones using poly A mRNA isolated from *T. spiralis* muscle stage larvae; however, the recombinant antigens were unable to detect antibodies to *T. spiralis* using sera from experimentally infected animals (D. S. Zarlenga and H. R. Gamble, unpublished data). Further, none of the genes coding for antigens described in the Abstract were shown to code for any of the ES products of *T. spiralis*, e.g., the 45, 49, and 53 kD immunodiagnostic antigens, (D. S. Zarlenga and H. R. Gamble, unpublished data).

SUMMARY OF THE INVENTION

The present invention comprises isolated DNA sequences which encode an amino acid sequence homologous to a segment of *Trichinella spiralis* 53 kD excretory-secretory antigen, the amino acid sequence having the capacity to bind antibodies made in a host to *T. spiralis*. Methods to obtain the sequences are also disclosed herein.

A further aspect of the invention is the provision of recombinant polynucleotide molecules containing the sequences. Such molecules include, for example, recombinant vectors, such as cloning or expression vectors, which contain a DNA sequence encoding an amino acid sequence homologous to a segment of *T. spiralis* antigen.

Another aspect of the invention is the provision of cells which are transformed by the above vectors or DNA sequences, as well as methods of producing *T. spiralis* antigen peptide molecules comprising growing such cells under conditions whereby a peptide comprising *T. spiralis* antigen is expressed and recovered.

A further aspect of the present invention is provision of purified antigenic material which has the ability to bind antibodies made in a host to *T. spiralis*, without cross reactivity with antibodies made to *Ascaris suum* or *Trichuris suis* (other common swine parasites) antigens. Use of the antigens of the invention in serodiagnostic tests and vaccines for trichinellosis is also disclosed herein.

A still further aspect of the invention is the provision of oligonucleotide probes capable of detecting the gene for *T. spiralis* antigen or fragment thereof and use of the probes to isolate DNA sequences encoding *T. spiralis* antigen. The DNA sequences which hybridize to the probes are encompassed by the present invention.

The invention represents the first successful cloning of an mRNA encoding a *T. spiralis* diagnostic antigen. The invention provides a means to produce *T. spiralis* antigen having desired purity and yield without the use of laboratory animals to maintain the parasites and without the use of expensive reagents needed for the isolation of the naturally derived protein.

A further advantage of the invention is that it can provide an unlimited source of standardized *T. spiralis* antigen.

Another advantage of the invention is that is provides *T. spiralis* antigen which has application as immunodiagnostic reagents or vaccines for trichinellosis.

Other objects and advantages of this invention will become readily apparent from the ensuing description.

GLOSSARY

For purposes of this invention, the following terms used herein have been defined below.

Cloning. The selection and propagation of (a) a vector containing one gene or gene fragment or (b) a single organism containing one such gene or gene fragment.

Codon. A DNA sequence of three adjacent nucleotides (a triplet) which codes (through mRNA) for an amino acid, a translational start signal or a translational termination signal. For example, the nucleotide triplets TTA, TTG, CTT, CTC, CTA and CTG encode for the amino acid leucine, TAG, TAA and TGA are translational stop signals, and ATG is a translational start signal.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eucaryotic mRNA. A polyadenylation signal and transcription termination sequence will usually be located 3' to the coding sequence.

DNA Sequence. A linear series of nucleotides connected one to the other by phosphodiester bends between the 3' and 5' carbons of adjacent pentoses.

Expression. The process undergone by a structural gene to produce a polypeptide. Expression requires both transcription of DNA and translation of RNA.

Expression Vector. A replicon such as a plasmid, virus, retrovirus, bacteriophage or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into RNA which is then in turn translated into the protein encoded by the coding sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promotor and ribosome binding and interaction sequences.

Heterologous DNA. An identifiable segment of DNA within a larger DNA molecule that is not found in association with the larger molecule in nature. Another example is a DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single-stranded regions of nucleic acids to form double-stranded molecules.

Nucleotide. A monomeric unit of ERA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U").

Oligonucleotide Probe. A nucleic acid fragment which will hybridize with complementary nucleic acid sequences, and thereby be useful for detecting specific nucleic acid fragments.

Phage or Bacteriophage. A virus which infects bacteria.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant".

Polypeptide. A linear series of amino acids connected one to the other by peptide bonds between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence GCTGGTTGTAAG may be translated via mRNA into three reading frames, each of which affords a different amino acid sequence:

GCT GGT TGT AAG-Ala-Gly-Cyc-Lys

G CTG GTT GTA AG- Leu-Val-Val

GC TGG TTG TAA A-Trp-Leu-(STOP)

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger ElNA sequence downstream of a promoter and upstream from a translational start sequence.

Replicon. Any genetic element (e.g., plasmid, chromosome, virus) that functions as an autonomous unit of DNA replication in vivo, i.e., capable of replication under its own control.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA ("mRNA") a sequence of amino acids characteristic of a specific polypeptide.

Transform. To change in a heritable manner the characteristics of a host cell in response to DNA foreign to that cell. A cell has been "transformed" by exogenous DNA when such exogenous DNA has been introduced inside the cell wall. Exogenous DNA may or may not be integrated (covalently linked) to chromosomal DNA making up the genome of the cell. In procaryotes and yeast, for example, the exogenous DNA may be maintained on an episomal element such as a plasmid. With respect to eucaryotic cells, a stably transformed cell is one in which the exogenous DNA has become integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription. The process of producing mRNA from a gene.

Translation. The process of producing a polypeptide from mRNA.

Vector. A replicon, such as a plasmid, virus, retrovirus, cosmid or nucleic acid sequence which is able to replicate in a host cell, characterized by one or a small number of restriction endonuclease recognition sites at which the sequence may be cut in a predetermined fashion. A vector can contain a marker suitable for use in the identification of transformed cells.

DETAILED DESCRIPTION OF THE INVENTION

The present invention provides purified *T. spiralis* antigenic polypeptide molecules homologous to a segment of *T. spiralis* 53 kD excretory-secretory antigen, the polypeptide molecules having the capacity to bind antibodies made in a host to *T. spiralis*. For purposes of this invention, the term "*T. spiralis* 53 kD ES antigen" and equivalent expressions are defined to mean the largest of the immunodominant ES proteins in the 40 to 55 kD range excreted and/or secreted by *T. spiralis* parasites. It has been reported that three immunodominant antigens appear in this range, having apparent molecular weights of 45,000, 49,000, and 53,000, and denoted as Ts.45 Ts.49, and Ts.53 antigens, respectively (Gamble and Graham, 1984, supra, and U.S. Pat. No. 4,670,384 to Gamble and Murrell, which is herein incorporated by reference). Although other investigators have reported the *T. spiralis* ES antigens in this range to have slightly different apparent molecular weights, e.g., proteins designated 48 kD and 50–55 kD by Silberstein and Despommier, 1984, supra, the ES antigen denoted as 53 kD can readily be identified in a western blot using monoclonal antibody ATCC HB 8678 as described in U.S. Pat. No. 4,670,384.

The phrase "homologous to a segment of *T. spiralis* 53 kD excretory-secretory antigen" further means an amino acid sequence sufficiently duplicative of the 53 kD antigen to allow possession of the unique biological property of being able to bind antibodies made in a host to *T. spiralis*, that is, immunologically reactive with sera from *T. spiralis*-infected animals.

The purified antigen of the invention differs from the naturally-derived 53 kD ES antigen as follows: it is essentially free of other endogenous parasite material; further, it is coded for by a *T. spiralis* mRNA of not greater than about 1250 bases. In contrast, the size of the native mRNA that codes for Ts.53 antigen is approximately 1350 bases.

In one embodiment, the purified antigen has no post-translational modifications, e.g., glycosylation, protein folding and the like. In another embodiment, antibodies to the polypeptide molecules do not cross react with Ts.45 or Ts.49 antigens.

It was unexpected that an immunogenic polypeptide molecule to the 53 kD ES antigen could be produced by recombinant techniques because, as discussed above, the 53 kD antigen has been reported to be a glycoprotein. It was believed that the primary in vivo antibody response was with glycosylated groups which are attached to the native protein and not with the primary or secondary structure of the protein. Further, as discussed above, previous attempts to produce recombinant DNA clones to the 53 kD (and 45 and 49 kD) antigens were unsuccessful.

Purified *T. spiralis* 53 kD antigen allows for the amino acid sequence to be determined, nucleic acid probes designed, and genes cloned. The purified antigen can be employed, for example, in immunediagnostic assays, e.g., ELISA, to diagnose *T. spiralis* in infected animals. In an ELISA test, purified 53 kD antigen is used as an antigen bound to wells of microtiter plates. Swine, human or other sera are then tested as described previously for ELISA testing for *T. spiralis* infection (Gamble et al., 1983, supra, and Gamble and Graham, 1984, supra).

Another use of the antigen is as a vaccine. In this use, the antigen is administered to an animal in an immunologically effective amount, that is an amount effective to immunize the animal against *T. spiralis*. The appropriate therapeutically effective dose can be determined readily by those skilled in the art. The antigen may be combined with a pharmaceutically acceptable carrier and may be administered by any method which enables the active ingredient to induce an immune responsed. The term "immunize" as used herein refers to partial or complete protection from infection as evidenced by reduced numbers of muscle larvae resulting from infection with *T. spiralis*.

The invention also encompasses DNA sequences which encode an amino acid sequence homologous to a segment of *Trichinella spiralis* 53 kD ES antigen. For purposes of this invention, the phrase "DNA sequence which encodes an amino acid sequence homologous to a segment of *Trichinella spiralis* 53 kD ES antigen" and equivalent phrases are defined to mean a DNA sequence which upon expression encodes an amino acid sequence of the *T. spiralis* 53 kD ES antigen which is of sufficient length and from a selected region or domain which is unique to the 53 kD ES antigen relative to other known proteins and sufficiently duplicative of the antigen to allow possession of the unique biological property of being able to bind antibodies made in a host to *T. spiralis*. Generally, the length of the unique domain is at least five amino acids; more generally, it is at least 10 amino acids; preferably it is at least 15 amino acids, and more preferably, it is 20 amino acids or more.

On the basis of the genetic code, there exists a finite set of nucleotide sequences which can genetically code for a given amino acid sequence. All such equivalent nucleotide sequences are operable variants of the disclosed sequences, since all give rise to the same protein, having the same amino acid sequence, during the course of in vivo transcription and translation. Consequently, all such variants are included in the scope of the present invention. DNA sequences which are substantially homologous to the selected region encoding 53 kD ES antigen are encompassed by the invention. Two DNA sequences are "substantially homologous" when at least about 85% (preferably at least about 90%, and most preferably at least about 95%) of the nucleotides match over the defined length of a selected region. Sequences that are substantially homologous can be identified in a Southern hybridization experiment under, for example, stringent conditions as defined for that particular system. Defining appropriate hybridization conditions is within the skill of the art. See, e.g., T. Maniatis et al., *Molecular Cloning: A laboratory Manual*, Cold Spring Harbor Laboratory, 1982; *DNA Cloning: A Practical Approach*, Volumes I and II (Ed. D. N. Glover) IRL Press, Oxford, 1985. It is also recognized that the general construction of the cloned gene may be varied considerably without altering the amino acid sequence of the encoded protein. The expression "sequence which encodes the 53 kD antigen" is intended to encompass all such variations.

A DNA sequence which encodes *T. spiralis* 53 kD antigen can be used to prepare recombinant DNA molecules by cloning in any suitable vector. The coding sequence can thereby be maintained in a composition substantially free of vectors that do not contain the coding sequence of the *T. spiralis* 53 kD gene (e.g., other library clones). A variety of vector-host combinations may be used. Vectors used in practicing the invention are selected to be operable as cloning vectors or expression vectors in the selected host cell. Numerous cloning vectors are known to those of skill in the art, and the selection of an appropriate cloning vector is a matter of choice. The vectors may, for example, be bacteriophage, plasmids, cosmids, phagemids, viruses, or hybrids thereof. Examples of recombinant DNA vectors for cloning and the host cells which they transform include bacteriophage λ (*E. coli*), pBR 322 (*E. coli*), pUC19 (*E. coli*), pBM-258 (Streptomyces), and pUC6 (Streptomyces). See generally, *DNA Cloning*, Volumes I and II, supra, and Maniatis et al., supra.

Within each specific vector various sites may be selected for insertion of the isolated DNA sequence. These sites are usually designated by the restriction enzyme or endonuclease that cuts them. The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art.

*T. spiralis* coding sequences may be inserted into the desired vector by known techniques. The recombinant vector is constructed so the the coding sequence is located in the vector with the appropriate control sequence and operationally associated therewith, that is, the positioning and orientation of the *T. spiralis* coding sequence with respect to the control sequences are such that the coding sequence is transcribed under the control of the control sequences (i.e., by RNA polymerase which attaches to the DNA molecule at the control sequences). The control sequences may be ligated to the coding sequence prior to insertion into a vector. Alternatively, the coding sequence can be cloned directly into an expression vector which already contains the control sequence and an appropriate restriction site downstream from the control sequence. The vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the *T. spiralis* sequence once inserted. The vector should be selected to provide a region which codes for a ribosomal binding site recognized by the ribosomes of the host cell into which the vector is to be inserted.

A number of procaryotic expression vectors are known in the art. See U.S. Pat. Nos. 4,652,525, 4,440,859, 4,436,815, and 4,342,832. A number of eucaryotic expression vectors have been described. See U.S. Pat. Nos. 4,546,082, 4,510,245, 4,446,235, and 4,443,540.

*T. spiralis* 53 kD antigen is produced by growing host cells transformed by the expression vectors described above under conditions whereby the antigen is produced. *T. spiralis* 53 kD antigen is then isolated from the host cells. The selection of the appropriate growth conditions and recovery methods are within the skill of the art.

The present invention also encompasses methods to obtain isolated DNA sequences having the characteristics described above. As discussed in detail below in Example 1, one method is to construct a cDNA expression library using polyadenylated messenger RNA isolated from *T. spiralis* muscle larvae. All *T. spiralis* cDNA sequences are inserted into DNA expression vectors to form recombinant expression vectors, and the recombinant expression vectors are inserted into suitable hosts to form transformants which express the DNA sequences into protein. These transformants are then screened with antibodies which are directed against *T. spiralis* antigens to thereby identify the sequences which code for antigens having the desired specificity, i.e., to identify clones expressing *T. spiralis* 53 kD antigen. In the preferred embodiment, the screening procedure has three levels. The first screening is carried out with immune pig serum to *T. spiralis*; the second screening is with sera from pigs experimentally infected with moderate levels of *T. spiralis* muscle larvae or rabbit antiserum to *T. spiralis* ES antigens, and the third screening is with polyclonal antibodies to monoclonal antibody purified 49 and 53 kD antigen. Isolated DNA sequences which encode *T. spiralis* 53 kD antigen may also be obtained by other methods, for example, by identification using an oligonucleotide probe capable of detecting a nucleotide sequence which codes for the antigen, as described below. A DNA coding sequence of the antigen can be prepared synthetically from overlapping oligonucleotides whose sequence contains codons for the amino acid sequence of the antigen. Such oligonucleotides are prepared by standard methods and assembled by procedures known to those is the art.

Oligonucleotide probes. Oligonucleotides probes can be prepared and used to isolate the desired *T. spiralis* antigen gene. The oligonucleotides are synthesized by any appropriate method. The particular nucleotide sequences selected are chosen so as to correspond to codons encoding an amino acid sequence of the antigen. Automated oligonucleotide synthesis has made the preparation of large families of probes relatively straightforward. While the exact length of the probe employed is not critical, generally it is recognized in the art that probes from about 15 to about 20 base pairs are usually effective. Longer probes of greater than 20 base pairs are also used.

The selected oligonucleotide probes are labeled with a marker, such as a radionucleotide or biotin using standard procedures. The labeled set of probes is then used in the screening step, which consists of allowing the single-stranded probe to hybridize to a suitable host previously transformed with vectors containing *T. spiralis* DNA sequences then denatured on nitrocellulose filters to expose the *T. spiralis* recombinant sequences to a suitable probe. The selection of the appropriate conditions is within the skill of the art. See generally *Nucleic Acid Hybridization*, Eds. B. D. Hames and S. J. Higgins (1985). The basic requirement is that hybridization conditions be of sufficient stringency so that selective hybridization occurs; i.e., hybridization is due to a sufficient degree of nucleic acid homology, about 70–75%, as opposed to nonspecific binding. Once a clone from a screened library has been identified by positive hybridization, it can be confirmed by methods such as restriction enzyme analysis and DNA sequencing that the clone contains a sequence that encodes an amino acid sequence homologous to a segment of *T. spiralis* 53 kD ES antigen.

Numerous issued U.S. Patents are available which disclose information useful to those skilled in the art in practicing the present invention. U.S. Pat. No. 4,710,463 to Murray discloses recombinant DNA expression vectors incorporating DNA sequences coding for a foreign polypeptide, e.g., Hepatitis B virus antigens, in a unicellular host. U.S. Pat. No. 4,440,859 to Rutter et al. discloses recombinant bacterial plasmids containing the coding sequences of higher organisms. U.S. Pat. No. 4,652,525 to Rutter et al. discloses isolation of a nucleotide coding sequence having the structure of the reverse transcript of an mRNA which encodes insulin, synthesis of double stranded DNA having the sequence, and transfer of the DNA to a host microorganism. U.S. Pat. No. 4,546,082 to Kurjan and Herskowitz discloses methods for expression of biologically useful heterologous polypeptides in yeast. U.S. Pat. No. 4,582,800 to Crowl discloses expression vectors which utilize transcriptional regulatory elements derived from bacteriophage lambda. U.S. Pat. No. 4,363,877 to Goodman and Seeburg discloses isolation of cDNA transcripts complementary to isolated mRNA, and recombinant DNA vectors containing codons for human somatomammotropin and for human growth hormone. U.S. Pat. No. 4,601,980 to Goeddel and Heyneker discloses the expression of a gene coding for human growth hormone in a pBR322/*E. coli* system. U.S. Pat. No. 4,590,163 to Helinski and Ditta discloses PK2 plasmids useful for gene cloning in gram-negative bacteria such as *E. coli*. U.S. Pat. No. 4,237,224 to Cohen and Boyer discloses methods for producing recombinant DNA expression vectors. U.S. Pat. No. 4,332,897 to Nakano et al. discloses lamboid bacteriophage vectors useful for transforming *E. coli*. U.S. Pat. No. 4,332,901 to Goldstein discloses a P4 derivative bacteriophage cloning vector. U.S. Pat. No. 4,704,362 to Itakura and Riggs and U.S. Pat. No. 4,356,270 to Itakura disclose recombinant plasmid vectors useful for transforming microbial hosts. U.S. Pat. No. 4,273,875 to Manis discloses a plasmid designated PUC6 useful as a cloning vector for transforming microbial hosts. U.S. Pat. No. 4,349,629 to Carey et al. discloses plasmid vectors employing the trp bacterial promoter useful as recombinant DNA expression vectors. U.S. Pat. No. 4,362,817 to Reusser discloses the plasmid pUC1060, which contains a tet gene promoter, useful as an expression vector. U.S. Pat. No. 4,599,308 to Hamer et al. discloses SV40 expression vectors which can be introduced into eukaryotic cells. U.S. Pat. Nos. 4,565,785 and 4,411,994 by Gilbert et al. discloses a recombinant DNA molecule having a bacterial gene and non-bacterial gene encoding a selected polypeptide. U.S. Pat. No. 4,795,805 by Itok et al. discloses antigen peptide to Adult T cell leukemia virus. U.S. Pat. No. 4,544,500 to Bittle and Lerner discloses antigens and vaccines useful in diagnosis and treatment of foot-and-mouth disease. The disclosures of all U.S. patent references cited herein are to be incorporated herein by reference.

The following examples are intended only to further illustrate the invention and are not intended to limit the scope of the invention which is described by the claims.

EXAMPLE 1

The following example describes the cloning, identification, and characterization of a DNA sequence that encodes an amino acid sequence homologous to a segment of *T. spiralis* 53 kD ES antigen.

A. Extraction of Total RNA.

*Trichinella spiralis* were maintained in female Sprague-Dawley rats by serial passage. Muscle larvae ($L_1$) were recovered 30–40 days after infection by pepsin-HCl (1% each) digestion of eviscerated, ground rat carcasses and washed by settling through several changes of water.

Total RNA was isolated from the recovered *T. spiralis* muscle larvae by guanidinium isothiocyanate: cesium trifluoroacetate isopynic centrifugation as described by D. S. Zarlenga and H. R. Gamble (*Analytical Biochemistry* 162: 569–574, 1987). In brief, approximately 1.5 million larvae ($10^9$ cells) recovered from four rats were concentrated by filtration and resuspended in 13 ml of 4M guanidinium isothiocyanate homogenizing solution (4M guanidinium isothiocyanate, 5 mM sodium citrate, 10 mM EDTA, 0.5% sarkosyl, 100 μM β-mercaptoethanol, 0.1% antifoam A) . The larval suspension was homogenized and centrifuged for 10 minutes at 3500×g. The cleared supernatant was transferred to a fresh tube and supplemented with cesium trifluoroacetate (Pharmacia-PL Biochemicals) (2.0 g/ml) to a final ratio of 1:1.6 homogenate:cesium trifluoroacetate. The final solution was separated into 5-ml polyallomer centrifuge tubes and spun at 200,000×g for 44 hours at 15° C. in an SW 55 Ti rotor. The DNA was removed by pipetting, immediately precipitated in 0.3M sodium acetate and 2 volumes of ethanol, and subsequently treated with proteinase K (200 μg/ml) at 37° C. for 30 minutes in 100 mM Tris, pH 7.5, 10 mM EDTA, 100 mM NaCl, and 0.5% w/v SDS. The balance of the gradient was aspirated down to the RNA band which was removed as a precipitate either by pipetting or "spooling" if sufficient amounts were present to do so. The RNA was washed with 70% ethanol (3×1.0 ml) and reddissolved in sterile TE (10 mM Tris, pH 7.6, 1 mM EDTA). No further purification was performed.

B. Isolation of Poly A mRNA.

Poly A mRNA was isolated by two successive passes of total RNA through an oligo(dT)-cellulose column essentially as described by Aviv and Leder (*Proc. Natl. Acad. Sci. USA* 69:1408–1412 (1972)). The poly A mRNA was eluted from the oligo(dT) cellulose column with sterile water preheated to 65° C. and then precipitated in 0.3M sodium acetate and 2.5 volumes of ethanol. The poly A mRNA was pelleted by centrifugation, washed with 80% ethanol, centrifuged once again, dried in vacuo, and dissolved in water.

C. Synthesis of Double Stranded cDNA.

Double stranded cDNA was generated from 10 μg of purified poly A mRNA according to the method of Gubler and Hoffman, *Gene* 25:63–269 (1983), as modified by Watson and Jackson, In: *DNA Cloning*, Volume I, Ed. D. M. Glover, IRL Press, Oxford, pages 79–88 (1985) using Eco RI linkers. In brief, first strand cDNA synthesis was carried out by priming with oligo dT in the presence of RNAsin, the appropriate dNTPs, and Moloney Murine Leukemia Virus (MMLV) reverse transcriptase. cDNA synthesis was stopped after 1 hour at 37° C. with EDTA, and the cDNA-RNA hybrid was extracted with phenol-chloroform, precipitated with ethanol and sodium acetate, centrifuged, dried in vacuo, and resuspended in water. Second strand synthesis was carried out in the presence of dNTPs and RNase H by DNA polymerase I. After a 1 hour incubation at 15° C. followed by a 1 hour incubation at 22° C., the reaction was halted and the double stranded cDNA was phenol-chloroform extracted, precipitated with ethanol and ammonium acetate, collected by centrifugation, dried in vacuo, and resuspended in 50 mM Tris, pH 7.6, 1 mM EDTA, 5 mM DIT. The cDNA was methylated with S-adenosyl-L-methionine by Eco RI methylase and the cDNA ends made blunt by treatment with T4 DNA polymerase in the presence of dNTP. After phenol-chloroform extraction, ethanol precipitation, centrifugation, and drying in vacuo, Eco RI linkers were ligated to the methylated cDNA termini using T4 DNA ligase and RNA ligase. The cDNA was then digested with Eco RI restriction enzyme for 1.5 hours at 37° C. to produce Eco RI compatible ends on the cDNA. The reaction was stopped with EDTA, phenol-chloroform extracted, ethanol precipitated, collected by centrifugation, dried in vacuo, resuspended in TE, and passed over a "NACS" column (Bethesda Research Laboratories). The cDNA was eluted in 2M NaCl in TE, ethanol precipated, collected by centrifugation, dried in vacuo, and resuspended in TE.

D. Preparation of Recombinant Bacteriophage λ DNA Using *T. spiralis* Double-stranded cENA.

Ten percent of the double-stranded cDNA was ligated to 1 μg of λgt11 arms containing compatible Eco RI ends using T4 DNA ligase at 4° C. for 16 hours.

E. Packaging of Recombinant Bacteriophage λgt11 DNA (cDNA Library Construction).

*T. spiralis* cDNA-bacteriophage DNA was packaged into intact virus particles using a "Packagene" extract following the procedures described by the manufacturer (Promega Biotech). After packaging, *E. coli* strain Y1090 was infected with the packaged cDNA library and plated onto Luria Broth (LB) agar plates in LB agarose containing 0.2% X-gal, 0.1 mM IPTG, and 100 μg/ml ampicillin. Using this technique, greater than 90% of the bacteriophage were observed to be recombinants (i.e., contained cDNA inserts) as judged by the percentage of white plaques of the total plaques obtained.

F. Identification of Recombinant Bacteriophages by Screening.

1. Preparation of Immune Sera. In order to screen the cDNA libraries, immune sera were generated by immunizing rabbits or swine with *T. spiralis* parasites, crude worm protein extract (CWE), or ES proteins. Individual rabbits were immunized subcutaneously with one of the protein preparations emulsified in Complete Freund's adjuvant and boosted two times further at 1 week intervals. Immune sera were collected after about 4 weeks. Swine were infected per os with 500 or 10,000 infective *T. spiralis* larvae and infection serum collected after 35 days. Serum from pigs with naturally acquired infection of *T. spiralis* were obtained according to Gamble et al., 1983, supra.

2. Immunoscreening of Recombinant Bacteriophages. Aliquots (approximately $10^5$ clones) of the *T. spiralis* bacteriophage libraries were used to infect and transform (transfect) *E. coli* Y1090 and plated as described in E above. (See R. A. Young and R. W. Davis, *Proc. Natl. Acad. Sci. USA* 80: 1194–1198, 1983, and *Science* 222: 778–782, 1983). The plates containing developing phage plaques were overlaid with nitrocellulose membrane disks which had been soaken in 10 mM IPTG and were incubated at 42° C. for 3 hours to induce production of the β-galactosidase fusion protein then transferred to 37° C. The nitrocellulose disks, impregnated with the *E. coli* proteins containing putative recombinant fusion protein, were removed from the plates after overnight incubation at 37° C., blocked in immunowash buffer (IWB) (0.15M sodium chloride, 50 mM Tris, pH 7.8, 0.05% Tween-20, and 5% non-fat dried milk), then screened overnight with a 1:200 dilution of serum from a pig experimentally infected with *T. spiralis* muscle larvae. Rabbit anti-swine IgG (1.0 μg/ml) and [$^{125}$I]-labelled goat anti-rabbit IgG ($2 \times 10^6$ cpm/filter) were used as second and third antibodies, respectively. Positive clones (antibody binding) were visualized by autoradiography and approximately 40–50 clones were picked and rescreened as described above using moderate dose swine infection sera (500 larvae/animal).

3. Five putative positives were picked and rescreened with rabbit antiserum to parasite ES antigen (diluted 1:200) followed by [$^{125}$I]-labelled goat anti-rabbit IgG ($2 \times 10^6$ cpm/filter). One of these clones showed strong hybridization in all the above screenings and was designated TsA-12.

G. Plaque Purification of Selected Bacteriophages in *E. coli* Y1090.

Figure 1:
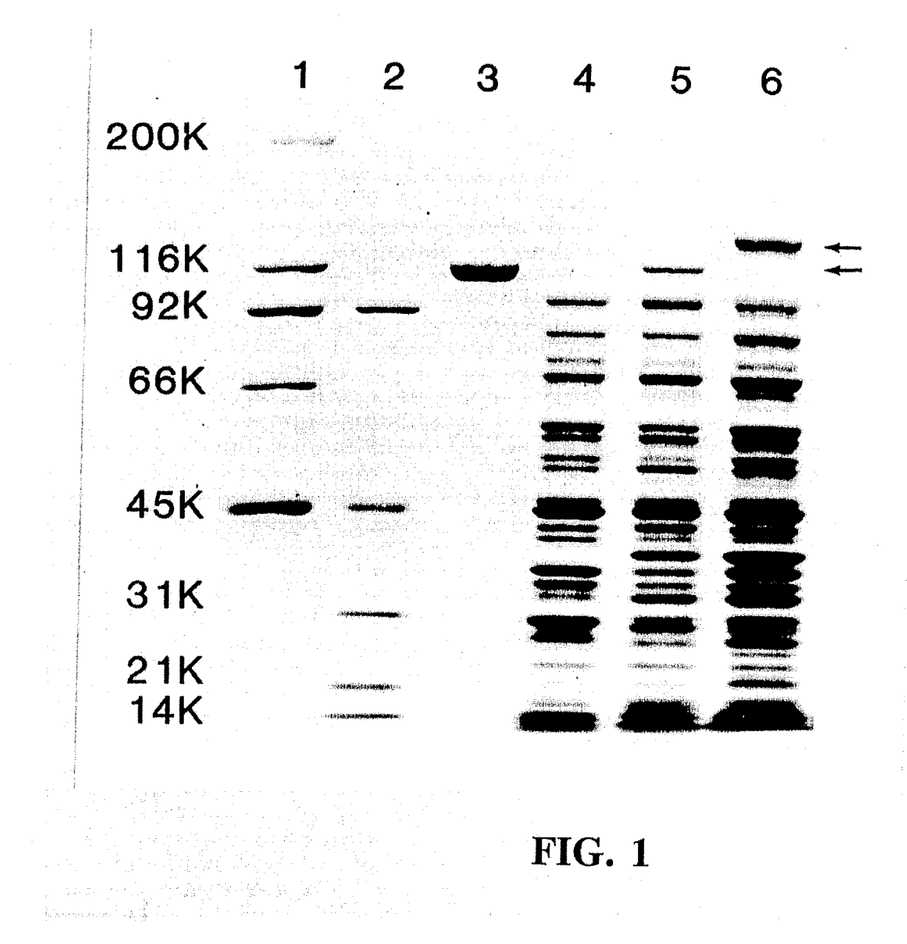
FIG. 1 shows a SDS-PAGE of TsA-12 bacterial lysates visualized by Coomassie blue staining. Arrows indicate the position of β-galactosidase (lane 5) and TsA-12 fusion protein (lane 6). Purified β-galactosidase (lane 3) and lysate from Y1089 bacterial cells (lane 4) were used as positive and negative controls, respectively. Lanes 1 and 2 are molecular weight markers.

Once identified and removed from the respective culture plate, positive bacteriophage TsA-12 identified in section F3 above was plaque purified by several rounds of plating, screening, and isolation as described above in section F2. This procedure was repeated until 100% of the plaques from the clone produced a positive signal upon immunoscreening. The molecular weight of the fusion protein was 140,000 daltons (FIG. 1).

H. Transfer of Selected Bacteriophages into *E. coli* Y1089 and Production of Fusion Proteins.

The titer of TsA-12 clonal bactariophage preparation prepared in section G above was determined by infecting *E. coli* Y1090 and plating on LB agar containing ampicillin. Individual aliquots of an overnight culture of *E. coli* Y1089 were infected at a M.O.I. equal to 10 with the bacteriophage cDNA clone and grown at 32° C. Individual colonies were picked into microtiter plates in a grid design and replica plated onto two LB agar-ampicillin culture plates. One inoculated plate was grown at 32° C., the other grown at 42° C. One colony growing at the lower temperature, but not at the higher temperature (indicative of a lysogenic state) was isolated. The *E. coli* strain Y1089 containing the TsA-12 insert has been deposited under the terms of the Budapest Treaty in the Agriculture Research Culture Collection (NRRL), Northern Regional Research Center, Agricultural Research Service, U.S. Department of Agriculture, Peoria, Ill., 60164, and has been assigned the accession No. NRRL B-18503. *E. coli*, strain Y1089 containing TsA-12 insert was grown in bulk culture in LB broth containing ampicillin at 32° C. When the O.D.$_{550}$ of the bulk culture reached 0.6–0.7, the temperature was shifted to 42° C. and held at that level for 30 minutes to induce the lytic cycle. After a temperature shift to 37° C., the culture was induced with 2 mM IPTG for 3 hours. The *E. coli* were then harvested by centrifugation at 3500 rpm for 10 minutes at 25° C. and the cell pellet was washed in phosphate buffered saline than resuspended in a volume of 0.05M Tris, pH 8, 10 mM MgCl$_2$, and 0.5 mM TPCK (N-tosyl-L-phanylalanine chloromethyl ketone) and PMSF (phenylmethylsulfonyl fluoride). The *E. coli* were lysed by treatment with 25 μg/ml lysozyme for 30 minutes on ice followed by freeze thawing and sonication for 20 seconds. The homogenate was treated with 5 μg/ml DNase for 30 minutes on ice and then centrifuged at $11,000 \times g$ for 15 minutes at 4° C. and the resulting supernatant stored at −20° C. for further analysis.

I. Purification of Fusion Proteins (TsA-12 Antigen).

The β-galactosidase fusion protein produced by the procedures described above was purified in the following manner. Bacterial lysogens were grown to an O.D.$_{550}$ of 0.6 and induced with IPTG for 3 hours and treated as described in section H above (See T. V. Huynh et al., In: *DNA Cloning*, Vol. I, (Ed. D. M. Glover), 49–88, IRL Press, Oxford, (1985)). Cell pellets were washed twice with 10 volumes of phosphate buffered saline (PBS) for 2 hours each time. Bacterial debris was collected after each wash by centrifugation and washed two additional times with 10 ml of 1.5% n-octyl-β-D-glucopyranoside (OGP). The final pellet was suspended in 6M urea, 10 mM dithiothreitol and agitated overnight to extract the recombinant antigen. Significant antigen remained in the pellet which could only be solubilized with 0.5% SDS.

J. Subcloning of Recombinant cDNA into pUC 19, Transformation of *E. coli* JM 83, and Production of Cloned Sequences Therefrom.

TsA-12 was subcloned into pUC 19 to facilitate further characterization by DNA mapping, DNA sequencing (J. Viera and J. Messing, *Gene* 19: 259–268, 1982), and Southern and northern blot hybridization. For subcloning procedures, see generally, Maniatis et al., 1982, supra. In the cloning of TsA-12 DNA, the Eco RI restriction sites were not regenerated; consequently, a Kpn I: Sst I digestion of recombinant bacteriophage DNA prepared according to Maniatis et al., 1982, supra, was required to remove the TsA-12 DNA (539 base pairs) from λ DNA along with approximately 1000 base pairs of λ DNA flanking each side of the insert. After having been purified by agarose gel electrophoresis, electroelution, and a "NACS" column, this entire gene segment was ligated into the expression plasmid pUC 19 in the Kpn: Sst I restriction site and used to transform competent *E. coli* bacterial cells, strain JM 83 using standard procedures. See, e.g., Hanahan, *J. Molec. Biol.* 166: 557, 1983. Plasmid DNA was generated as described by C. Sadhu and L. Gedamu, *Biotechniques* 6:

20–21, 1988, are the cDNA insert isolated by restriction enzyme digestion as outlined above.

K. Characterization of TsA-12 Antigen.

1. For labeling and hybridization studies, plasmid DNA was digested with Eco RI, electrophoresed on LMP agarose (FMC), and the insert DNA band was excised, placed in electrophoresis buffer in dialysis bags and electroeluted for 2 hours at 100 volts. The dialysate was purified over a NACS column and the DNA precipitated with ethanol and sodium acetate. The insert DNA was labeled with 100 μCi of $^{32}$P-alpha dCTP (3000 μCi/mMole, New England Nuclear) by nick translation, Rigby et al., *J. Molec. Biol.* 113: 237, 1977, using DNase I and DNA polymerase I (BRL). Labeled DNA was separated from $^{32}$P-dCTP by spun column chromatography as described by Maniatis et al., 1982, supra. *T. spiralis* muscle larvae DNA was purified as described by J. B. Dame and T. F McCutchan, *Molecular and Biochemical Parasitology* 8: 263–279, 1983. The purified DNA (10 μg) was digested with 50 units of either Hind III, Pst I, Sal I Eco RV, Xba I or Eco RI restriction enzymes (BRL), electrophoresed in 0.8% agarose (FMC) and transferred to "Nytran" membrane using Southern blotting procedures. See E. M. Southern, *Journal of Molecular Biology* 98: 503–517, 1975. After transfer, the DNA-blotted 37 Nytran" paper was baked in vacuo at 80° C. for 2 hours, prehybridized with 0.5M NaCl, 0.05M sodium citrate, pH 7.0 (6X SSC), Denhardt's solution, and 0.2% sodium dedecylsulfate (SDS) for 6 hours at 65° C., and hybridized with $10^6$ cpm of $^{32}$P-labeled probe for 16–20 hours at 65° C. The blots were washed three times with 0.2X SSC, 0.1% SDS at 50° C. for 30 minutes per wash. The blots were air dried and overlaid with photographic film (Kodak XAR) to visualize the hybridization patterns. Northern blots were similarly generated using 10 μg of total RNA isolated from *T. spiralis* infective muscle larvae ($L_1$), newborn larvae (C. H. Wang and R. G. Bell, *Parasite Immunology* 10: 293–308, 1988), or adult parasite (Wang and Bell, supra), and separated on a 1% denaturing formaldehyde gel as described by L. G. Davis et al., *Basic Methods in Molecular Biology*, Elsevier Science Publishing Co., Inc., 1986. After separation on 1% agarose the RNA was transferred to nitrocellulose and screened with insert TsA-12 cDNA as described above for Southern blot analysis.

The foregoing techniques revealed that the TsA-12 cDNA insert cloned in pUC 19 ENA was 539 bp in length and likely contains introns within the genome. Northern blots of RNA from *T. spiralis* infective larvae, newborn larvae, and adult parasite indicate that the TsA-12 gene is expressed within the ($L_1$) and adult stages only.

2. Preparation of Rabbit Antisera. Rabbits were immunized with recombinant antigen from the induced lysogen that was separated from other bacterial proteins by sodium dodecyl sulfate-polyacrylamide gel electrophoresis (SDS-PAGE). Fusion protein was excised from the gel, then emulsified in Freund's incomplete adjuvant and injected subcutaneously on days 1 and 8. A third immunization was given on day 15 in the ear vein in the absence of adjuvant using fusion protein that had been allowed to diffuse from gel slices for 24–48 hours prior to injection. Rabbits were bled 5 days later by heart puncture.

3. Western Blot Analysis. The TsA-12 lysogen was induced with IPTG and the fusion protein purified as described above in sections H and I. Purified or crude protein samples (1–10 μg) were boiled in SDS sample buffer for 5 minutes and electrophoresed on 10% SDS-polyacrylamide gels (U. K. Laemmli, *Nature* 227: 680–685, 1970). Separated proteins were either stained with Coomassie blue or electrophoretically transferred to nitrocellulose (H. Towbin et al., *Proc. Nat. Acad. Sci. USA* 76: 4350–4354, 1979), then blocked in IWB and incubated overnight with a 1:200 dilution of rabbit antiserum to either antibody-purified Ts.49, Ts.53 ES antigens, purified TsA-12 fusion protein or β-galactosidase. The next day, the filters were washed in IWB and IWB containing 1% Triton-X 100 and 0.1% SDS then incubated with peroxidase-labelled goat anti-rabbit IgG (0.2 μg/ml) for 3–4 hours. Bound enzyme was visualized by the addition of $H_2O_2$ and 4-chloro-1-napthol (Kirkegaard and Perry).

Figure 2:
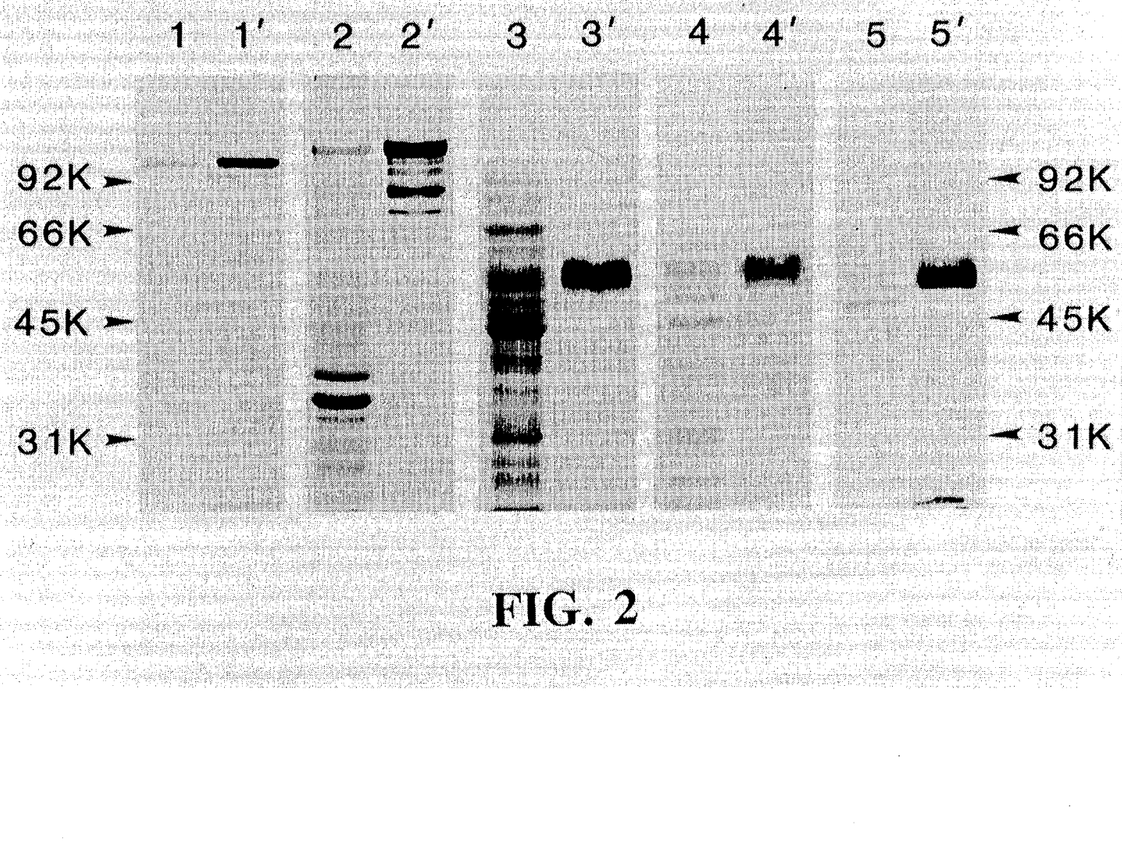
FIG. 2 shows a western blot analysis of purified TsA-12 fusion protein and *T. spiralis* antigens with rabbit antiserum to TsA-12 fusion protein. Protein samples were boiled in SDS-sample buffer, separated on 10% SDS-polyscrylamide gel and visualized by Coomassie blue staining (lanes 1–5) or blotted to nitrocellulose and screened with rabbit anti-TsA-12 serum (lanes 1'–5'). Lanes 1 and 1', purified β-galactosidase; lanes 2 and 2', TsA-12; lanes 3 and 3', crude worm extract (CWE); lanes 4 and 4', ES protein; and lanes 5 and 5 ', monoclonal antibody affinity-purified Ts. 49 and Ts.53 antigen FIGS. 3A and B show a western blot analysis of β-galactosidase (lanes 1, 1'), TsA-12 (lanes 2, 2'), and ES proteins (lanes 3, 3') using rabbit antiserum to monoclonal antibody-purified Ts.49 and Ts.53 antigens. Protein samples were denatured by boiling in SDS-sample buffer, separated on a 10% SDS polyacrylamide gel, then either stained with Coomassie blue (lanes 1, 2, and 3) or screened with rabbit anti-Ts49, Ts53 serum (lanes 1', 2', and 3').
Figure 3:
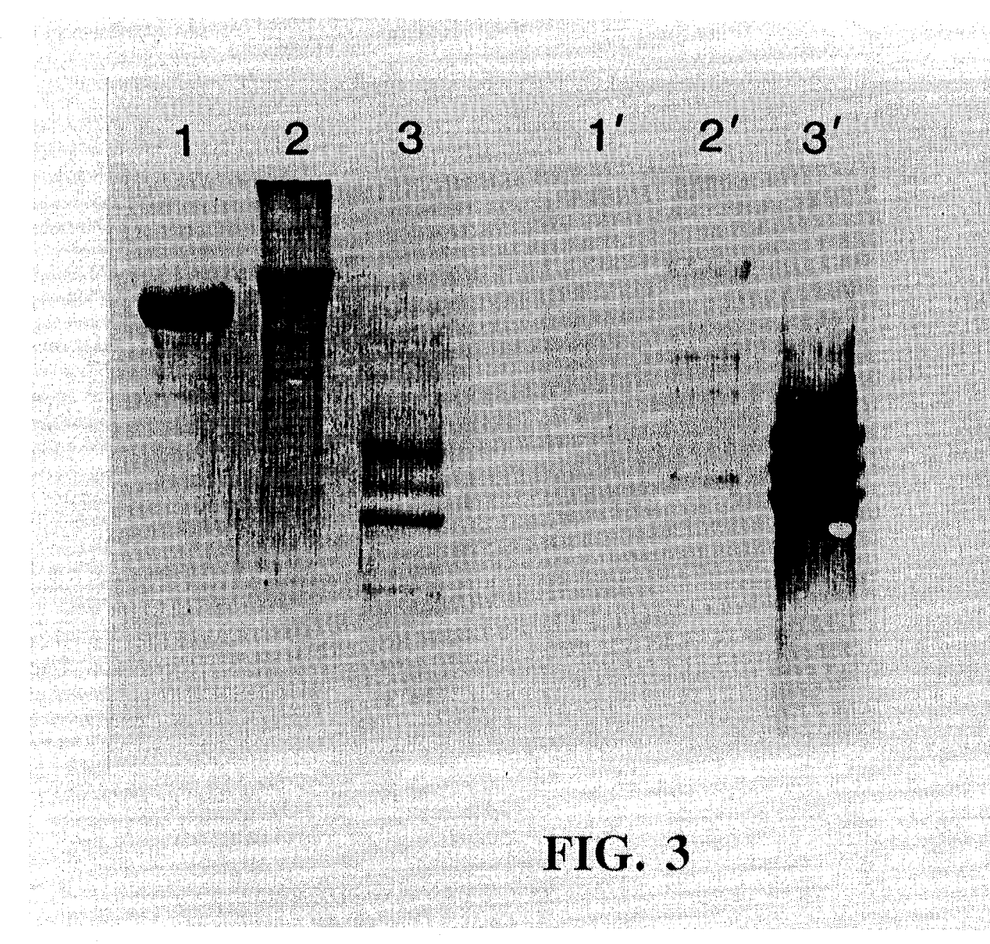

Rabbit antibodies raised against fusion protein TsA-12 that had been purified by polyacrylamide gel electrophoresis were used to screen western blots of *T. spiralis* muscle larvae crude worm extract (CWE), total ES protein, and monoclonal antibody affinity-purified Ts.49 and Ts.53 antigens. In all cases, rabbit anti-TsA-12 serum reacted exclusively with a doublet in the 53,000 molecular weight range as well as with the fusion protein and β-galactosidase positive controls (FIG. 2). Repeat screenings failed to generate antibody binding to other ES antigens. In addition, no binding was observed when TsA-12 antiserum was used to screen adult CWE or ES proteins. This specificity for Ts.53 antigen with no cross reactivity to the Ts.49 or Ts.45 antigens was unexpected. It had been believed that the same gene coded for the 45, 49, and 53 kD ES antigens. This was based on similarities in antibody binding to the naturally derived antigens (Gamble and Graham, 1984, supra). Our results suggest that separate mRNA species may be involved in the production of the 45, 49, and 53 kD ES antigens. Rabbit antiserum to affinity-purified antigens Ts.49 and Ts.53 was used to screen western blots of TsA-12 fusion protein, ES antigen, and β-galactosidase (FIG. 3). This antiserum bound to antigens Ts.45, Ts.49, and Ts.53 in ES preparations; binding was also observed with the 140,000 molecular weight TsA-12 fusion protein with less intense binding to several lower molecular weight bands in the TsA-12 preparation at 48,000, 66,000, and 95,000 molecular weight. No binding to purified β-glactosidase was observed using antibodies to purified ES antigens.

4. ELISA with TsA-12 Fusion Protein. The specificity of TsA-12 for *T. spiralis* infection was evaluated by ELISA using sera from pigs experimentally infected with *Ascaris suum, Trichuris suis* or *T. spiralis*. Purified TsA-12 fusion protein was diluted to 5 μg/ml in 0.1M carbonate buffer (pH 9.6) and bound to microtiter plates. Sera from pigs experimentally infected with *A. suum, T. suis,* or *T. spiralis* were diluted 1:100 in PBS containing 0.05% Tween-20 and 100 μl was added to wells for 30 minutes. Rabbit anti-swine IgG (1 μg/μl) and peroxidase labelled goat anti-rabbit IgG (0.1 μg/μl) were used as second and third antibodies, respectively. Bound enzyme was quantitated by the addition of $H_2O_2$ and 2′,2′-azine-di[3-ethyl-benzthiazoline sulfate] (ABTS) (Kirkegaardand Perry).

The results are tabulated in Table 1 below. An optical density ratio greater than 4:1 (0.176:0.039) was obtained for *T. spiralis* infection serum as compared to normal serum controls (0.039) whereas no optical density values above normal serum controls were observed with *A. suum* (0.027) or *T. suis* (0.037) infection sera.

TABLE 1

Recognition of TsA-12 by Pigs Infected With *T. Spiralis* or Other Swine Parasites

| Serum | ELISA (O.D.) | P/N Ratio |
|---|---|---|
| Uninfected Pig | .039 | — |
| *T. Spiralis* Infected Pig | .176 | 4.5 |
| *Ascaris Suum* Infected Pig | .027 | <1.0 |
| *Trichuris Suis* Infected Pig | .037 | <1.0 |

To determine the kinetics of antibody responses to TsA-12, a group of 25 Swiss-Webster mice were each orally inoculated with 150 *T. spiralis* muscle larvae. Serum was collected from 5 uninoculated mice on day 0 and 5 infected mice on days 7, 14, 21, 28, and 35 post-inoculation. Collected sera was diluted 1:100 and tested by ELISA using 1 μg/ml TsA-12 to coat plates. Goat anti-mouse IgG and IgM ( 1.0 μg/ml ) and peroxidase labelled rabbit anti-goat ( 0.1 μg/ml) (both Kirkegaard and Perry) were used as second and third antibody reagents. ABTS substrate was used as described above.

Figure 5:
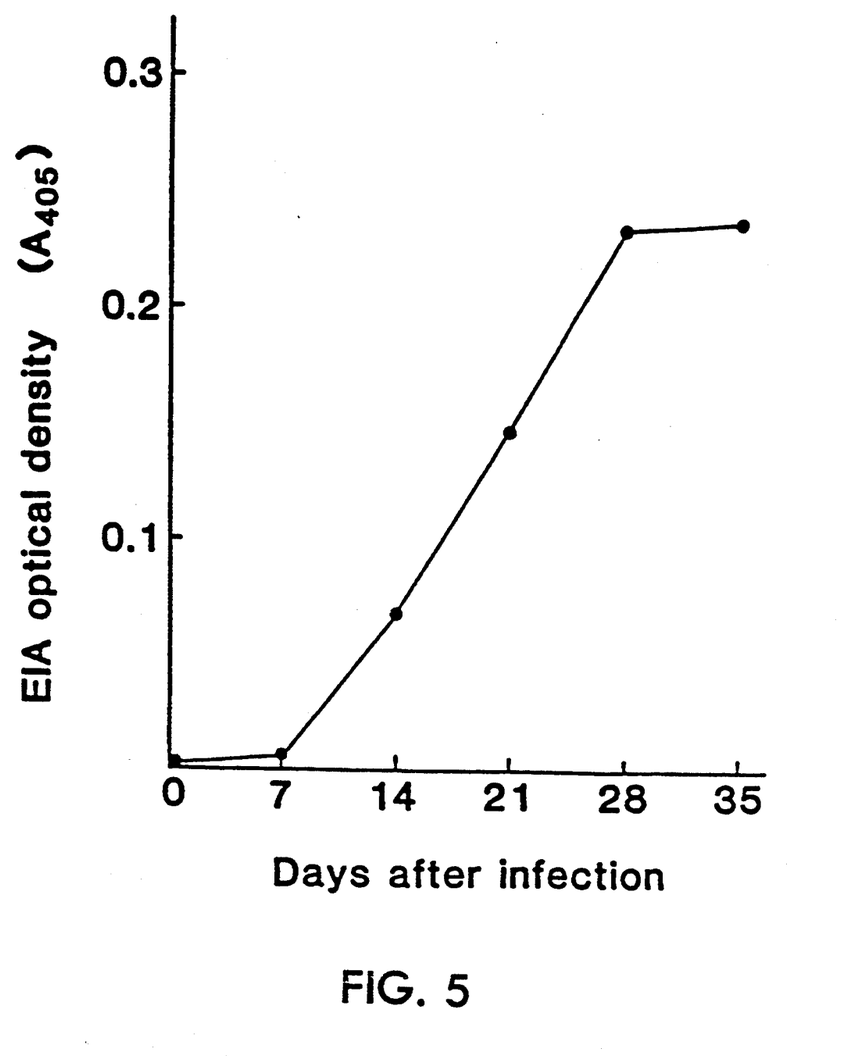
FIG. 5 shows ELISA detection of antibodies to TsA-12 in mice inoculated with 150 *T. spiralis* muscle larvae and bled at various times after inoculation. Background absorbance readings from uninoculated mice were subtracted from all ELISA readings.

Mice inoculated with *T. spiralis* $L_1$ developed an antibody response to TsA-12 as early as 14 days post inoculation. Antibody levels increased over time and peaked at 28-35 days post inoculation (FIG. 5).

5. Immunoperoxidase Staining. Rabbit anti-TsA-12 serum was used to localize the homologous *T. spiralis* antigen by immunoperoxidase staining. Tissue sections from infected mice were screened with either anti-TsA-12 serum or rabbit anti-β-galactosidase serum as a negative control as follows. Tongue tissue removed from mice 30–40 days post-infection with *T. spiralis* muscle larvae was fixed in 4% glutaraldehyde and dehydrated through a series of washes of increasing ethanol concentration. Tissue was embedded in paraffin and sectioned at 5 μm then mounted on slides which were cleared with xylene and rehydrated. Sections were incubated with a 1:1000 dilution of either rabbit anti-TsA-12 or rabbit anti-β-galactosidase sera. Slides were washed and processed using the "Vectastain" ABC immunoperoxidase kit (Vector laboratores) according to the manufacturer's protocol, then counterstained with Harris hemotoxylin for 30 seconds. Slides were washed in tap water then photographed.

Figure 4A:
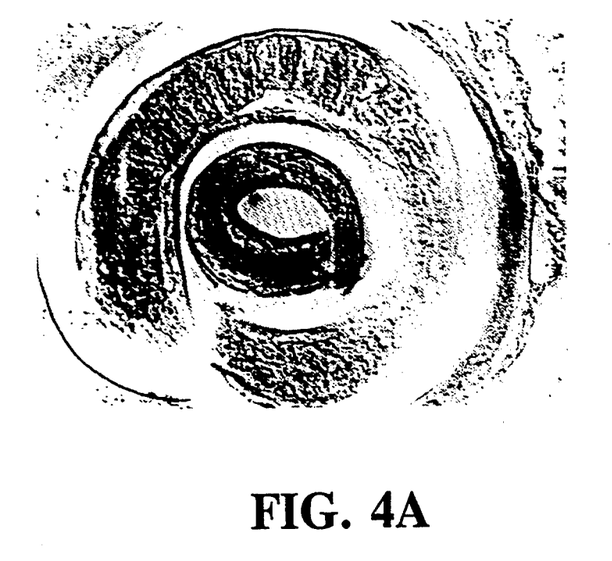
FIGS. 4A and B show immunoperoxidase staining of *T. spiralis* muscle larvae from infected mouse tongue. Deparaffinized and hydrated tissue sections were incubated overnight with a 1:1000 dilution of rabbit anti-β-galactosidase serum (A) or rabbit anti-TsA-12 serum (B), then visualized using the "Vectastain" ABC immunoperoxidase staining kit. Arrows indicate regions of stichocyte where TsA-12 antibody bound antigen.
Figure 4B:
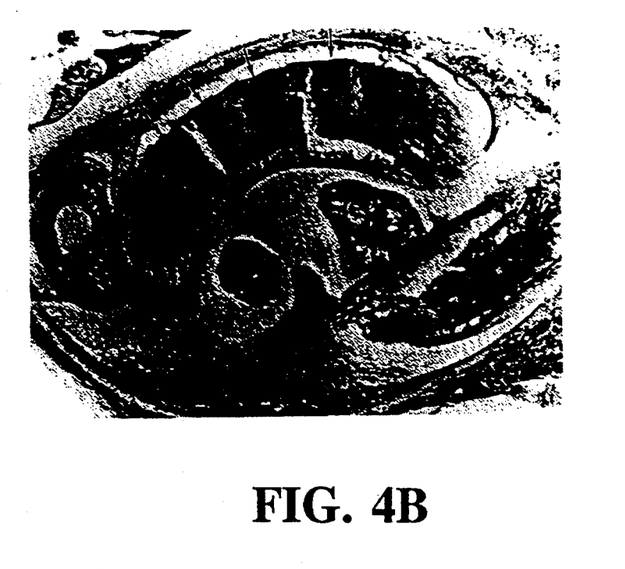

FIG. 4 shows immunoperoxidase staining of *T. spiralis* muscle larvae from infected mouse tongue. The most intense staining with TsA-12 antiserum was localized within the stichocyte cells of the muscle larvae (FIG. 4B). Control antiserum to β-galactesidase did not stain parasite sections (FIG. 4A).

L. DNA Sequencing of TsA-12.

The DNA sequence of the cDNA insert TsA-12 was determined using the dideoxy chain termination technique (F. Sanger et al., *Proc. Nat. Acad. Sci. USA* 74, 5463, 1977). For single stranded sequencing, purified cDNA insert was obtained in accordance with section J above, ligated into Kpn I: Sst I digested M13mp18 and M13mp19, and used to infect and transform JM101 cells (See J. Messing, *Methods Enzymol.* 101: 20, 1983). White colonies were picked and used to generate single stranded viral DNA for sequencing; where possible, double stranded sequencing was performed directly in pUC 19 plasmid DNA as described by Kraft et al., *BioTechniques* 6:544–546 (1988) using $^{35}$S-dATP (NEN 500 Ci/mMole) and the "Sequenase" Reaction kit (US Biochemicals), and analyzed on a 6% polyacrylamide sequencing gel. The complete TsA-12 sequence of M13 recombinant viral DNA and pUC double stranded plasmid DNA insert was ascartained. The sequence of cDNA clone TsA-12, as determined by these procedures, is shown in Table 2 below.

TABLE 2

DNA SEQUENCE OF TsA-12 CODING STRAND

| | | | | |
|---|---|---|---|---|
| 5'TTTTTTTTTT | TTTTTGTTTT | TTACAGTTTG | AAAAACTTTA | CTGATAGATA |
| GATTGCTTAA | AGAAGCTATA | ATTTCTGCTG | GATTTAGAAC | AACAACTGTA |
| GTTCTGAAAA | AACATGTTGG | AAAAACCCTT | TTGGGGGCTT | TGGTTTGCGC |
| TTTAAACGTA | GTGCCGATTT | ATCGCCTCCT | TCCAACCAAT | CTGAATGTTT |
| CCATCACTGG | GAAATTTATC | AATGCTGCCA | ATGTGCTCTT | TGTTTTCATC |
| GAACACTCCG | GCTACTTCAG | TTATTACGTA | AGCATCGTCC | GTATCATTCG |
| GTGTTGCTCT | GTGTTTAACT | TTAGTGCTAA | TTGTTGCATT | GTACAGCTTT |
| TGAAGTTTAT | CTTCTTTGTC | AGAATTGCTT | AATTCCATGG | TATCAAAAGC |
| TTTTCTTAAA | ATACGATCTA | TTTCATCACC | AAATGGCTTC | TGAATTGGAT |
| TTGTAACAAA | AACTTCGGGA | TTTCTATTGA | ATCATTTGCA | TTTATAAGAG |
| ATAGAACCTC | AGTAGTTTTA | CCATTTTTCC | TGAAAATAG | |

←Probable Reading Frame

DNA sequencing of the TsA-12 insert revealed the long poly A tail corresponding to the 3' end of the messenger RNA and a single Hind III restriction site consistent with restriction studies done on this clone. To the extent of any discrepancies between the sequence shown above and the sequence contained in the deposited clone, the latter is controlling.

EXAMPLE 2

The following example illustrates the use of antigens of the invention as a diagnostic reagent.

The ELISA test for swine or humans infected with *T. spiralis* uses as antigen a preparation of ES product or purified antigens Ts.49 and Ts.53 (Gamble et al., 1983, supra; Gamble and Graham, 1984, supra). The 53 kD antigen of the invention is used in place of these other antigen preparations as follows: the 53 kD antigen diluted to an appropriate concentration in carbonate buffer (pH 9.6) is used to coat wells of a 96-well microtiter plate. After coating and between all antibody steps wells are washed three times with phosphate-buffered saline (PBS) containing 0.05% Tween 20. Swine or human senram (diluted in PBS-Tween) is then added to the wells and incubated for 30 minutes. After washing, a second antibody (goat anti-swine or goat anti-human, conjugated to an enzyme) diluted in PBS-Tween is added and incubated for another 30 minutes. After a final washing a suitable enzyme substrate is added and the color change read on a microtiter plate reader. Positive results are determined as recorded in Table 1.

EXAMPLE 3

The following example illustrates the use of antigens of the invention as a vaccine.

*T. spiralis* ES antigens and purified Ts.49 and Ts.53 have been used to immunize mice and pigs against challenge infection with *T. spiralis* (Gamble, 1985, supra). As a vaccine, the 53 kD antigen of the invention is used in the same protocol as follows: antigen at an appropriate concentration is emulsified in Freund's complete adjuvant and administered intraperitoneally to animals on days 0, 14, and 28. In experiments using ES antigens or Ts.49 and Ts.53 both mice and pigs were stimulated to produce an effective immune response to challenge infection. In a preliminary experiment, immunization of mice with 1 μg doses of recombinant 53 kD antigen (TsA-12 antigen) prepared as described in Example 1 above induced a 48.3% level of immunity. In related studies, pigs immune to *T. spiralis* infection had T-cells which were immunoreactive to the 53 kD antigen.

It is understood that the foregoing detailed description is given merely by way of illustration and that modification and variations may be made therein without departing from the spirit and scope of the invention.

We claim:

1. An isolated DNA sequence consisting of a DNA sequence encoding only the amino acid sequence encoded by the DNA sequence of table 2.

2. The isolated DNA sequence of claim 1 wherein said sequence is said TsA-12 DNA coding sequence.

3. A vector containing the DNA sequence of claim 1 inserted therein.

4. The vector of claim 2, said vector having a promoter and said DNA sequence is inserted in said vector downstream of said promoter and operatively associated therewith.

5. The vector of claim 3, further comprising a region coding for the production of β-galactosidase.

6. A transformed cell comprising a host cell containing the isolated DNA sequence of claim 1 inserted therein, and wherein said transformed cell is effective for the production of said amino acid sequences in nonglycosylated form.

7. The transformed cell according to claim 6 wherein said host cell is a procaryotic cell.

8. The transformed cell according to claim 7 wherein said cell is a bacterial cell.

9. The transformed cell according to claim 8 wherein said cell is a *Escherichia coli*.

* * * * *